(12) United States Patent
Nachaliel (10) Patent No.: US 9,351,690 B2
(45) Date of Patent: May 31, 2016

(54) IMAGING SYSTEM (71) Applicant: Ehud Nachaliel, Mitzpeh Netofa (IL)

(72) Inventor: Ehud Nachaliel, Mitzpeh Netofa (IL)

(73) Assignee: CMT MEDICAL TECHNOLOGIES LTD., Yokneam Ilit (IL)

(*) Notice: Subject to any disclaimer, the term of this patent is extended or adjusted under 35 U.S.C. 154(b) by 31 days.

(21) Appl. No.: 13/958,714

(22) Filed: Aug. 5, 2013

(65) Prior Publication Data

US 2015/0036797 A1 Feb. 5, 2015

(51) Int. Cl.
*A61B 6/14* (2006.01)
*A61B 6/00* (2006.01)
*H01J 35/32* (2006.01)
*B82Y 15/00* (2011.01)
*H05G 1/10* (2006.01)

(52) U.S. Cl.
CPC ............... *A61B 6/145* (2013.01); *A61B 6/4057* (2013.01); *B82Y 15/00* (2013.01); *H01J 35/32* (2013.01); *H05G 1/10* (2013.01); *Y10S 977/742* (2013.01); *Y10S 977/919* (2013.01); *Y10S 977/939* (2013.01); *Y10S 977/95* (2013.01)

(58) Field of Classification Search
CPC .................................. A61B 6/14; A61B 6/145
See application file for complete search history.

(56) References Cited

U.S. PATENT DOCUMENTS

| 5,729,583 | A | * | 3/1998 | Tang et al. ..................... 378/122 |
| 5,973,444 | A | | 10/1999 | Xu et al. |
| 6,553,096 | B1 | | 4/2003 | Zhou et al. |
| 2007/0161885 | A1 | * | 7/2007 | Kimchy ......................... 600/407 |

* cited by examiner

*Primary Examiner* — Hoon Song
(74) *Attorney, Agent, or Firm* — William Dippert; Laurence Greenberg; Werner Stemer (57) ABSTRACT

An intraoral radiation device comprises a biocompatible intraoral receptacle with an X-ray source therein.

9 Claims, 11 Drawing Sheets

IMAGING SYSTEM

FIELD OF THE INVENTION

The present invention relates to a miniature intraoral X-ray imaging system.

BACKGROUND OF THE INVENTION

X-ray imaging at the dentist takes one of three major forms: static images, mostly done as a part of the dental checkup ("status"), panoramic imaging, where a panoramic view of the whole mouth results and "cone-beam computerized tomography" (CBCT) imaging, where volumetric information of the mouth is collected, reconstructed and displayed.

Static imaging is ordinarily performed using the clinics' x-ray source and intraoral film or an intraoral digital flat panel detector (FPD). The three most used scan geometries are: Bitewing scan, which shows the crown portions of the top and bottom teeth together; Periapical scan, which shows one or two complete teeth from crown to root, and Palatal or Occlusal scan, which shows the roof or floor of the mouth. In Bitewing and in Periapical scans the dentist inserts the radiographic film or FPD into the patient's mouth and fixes it behind the area of interest (ROI). Then, the dentist approaches the x-ray source, mounts it externally against the ROI and shoots the x-ray. The film then has to be developed, or the information from the FPD be uploaded to a host system for display.

A more sophisticated x-ray system is used for panoramic imaging. It has a rotating arm, carrying the x-ray source on one end and the FPD on the other end (the following assumes that FPD is used, not a film). The patient's head is positioned within chin, forehead and side rests, and is coaxial to the rotating arm. The patient is also provided with a bite blocker to prop open the oral cavity. Exposure is performed while the source and the FPD continuously rotate around the patient head. A set of discrete images is thus obtained, which capture different sections of the mouth. Next, a specialized algorithm stitches the images together, resulting a single, flattened image of the mouth.

CBCT imaging is done in a similar manner, where the system takes many "views" around the patient. However, in this case, it reconstructs the measured data, thus resulting in a 3-dimensional representation of the mouth.

An important factor of any imaging modality is the spatial resolution. The resolution depends both upon the size of the radiation source (as expressed in the beam's spot-size) and the image sampling spacing (in FPD it is the pixel pitch). The various methods of static imaging all require high resolution (for visualizing the fine details of the gums and teeth)—typically of about 30 µm size. For panoramic imaging the resolution is typically 150 µm, and for CBCT it is about 250 µm. A film is sometimes still being used for static imaging, because films have an intrinsically high spatial resolution.

Alternatively, if an intraoral FPD is used, it must have the required pixel pitch of about 30 µm, comparable with film resolution. For panoramic scans, the source size is about 300 µm, while the FPD pixel is about 100 µm. Therefore, the FPD is kept closer to the patient head, for bringing the resolution closer to the required 150 µm. CBCT utilizes the same source and FPD as in the panoramic imaging system; however, the FPD can be mounted farther away from the patient and the resolution is, accordingly, lower.

While CBCT is considered the "high-end" of the dentistry imaging and is used only for full mouth reconstruction, the static and panoramic imaging methods are much more common. Yet, they suffer from major technological drawbacks: Static imaging requires multiple exposures. For example, four bitewing scans and 10-17 Periapical scans are taken in a typical checkup meeting. The mounting in and out of the imager is unpleasant both to the patient and to the dentist. In addition, the whole process is time consuming, which includes the times of fixing the FPD inside the patient's mouth, mounting the x-ray tube, moving behind an x-ray shield, performing the exposure and reading the resulting image.

Panoramic viewing is faster and more convenient. However, the method of encompassing the patient's head necessitates radiation exposure to extraoral tissues, notably the patient's spine. Therefore, the absorbed dose for the patient is considerably higher than required for sheer imaging of the mouth. Furthermore, the image quality deteriorates, because the spine casts a shadow on the front teeth. A higher voltage x-ray setting (typically 80 kVp and more) is also required in order for the beam to pass through the spine, which reduces the contrast between the teeth/bones and the soft tissues (gums). Yet a further problem is that the magnifications of the images vary as the system performs the scan, because both the source-to-tooth-distance and the FPD-to-tooth-distance change as the FPD and tube move around the patient head. Therefore, neighboring images have different magnifications on their edges, resulting in blurring of the stitched image.

One partial solution to the panoramic drawbacks is described in U.S. Pat. No. 4,176,278. An intraoral x-ray source based upon an encapsulated nuclear source is disclosed, which is connected through a gears-and-pulleys system to a film holder. The device fixes the magnification, thus eliminating the need in moving the source and the patient head. However, the use of a nuclear source necessitates arrangements of storing and transferring it within the clinic. Furthermore, the sources decay and require frequent replacements. The complicated mechanical device makes the filming apparatus cumbersome and expensive and makes the filming itself much more difficult. Finally, none of the problems of static imaging are solved.

U.S. Published Patent Application No. 2013/0010923 describes another intraoral radiation type X-ray imaging system for capturing an X-ray image of teeth or a jawbone that includes: a tubular X-ray generating unit (having a electron-emitting source, an X-ray emitting source and a collimator) placed in the oral cavity; a high-voltage source providing power for the X-ray generating unit; an X-ray detection unit, and an X-ray generating unit support to control the position of the X-ray generating unit in the oral cavity.

In U.S. Published Patent Application No. 2013/0010923 the high-voltage source is described as positioned outside of the mouth. This setup requires high-voltage cabling that goes between the jaws, making the important Bitewing (i.e., teeth pressed together) imaging impossible. In addition, even the option of threading the cabling through the unit support, as described therein, might also pose a safety issue, and is certainly a cause for concern, since the 100 kVp cables are being bitten and moistened by the patient. Moreover, since the collimator absorbs much of the X-ray radiation, the required current is as high as 15 mA.

Also described therein is rotation of the detector around the mouth, the intraoral source following the detector. However, the source is mounted on a shaft going from the inside to the outside of the patient mouth. This arrangement also disallows any imaging with teeth pressed together.

The described x-ray source emits the radiation to all directions (more than 180°). Accordingly, for panoramic scans, the angular acceptance may be limited by a collimator that is possibly rotated to the desired orientation. However, this arrangement is also impractical because the emitted radiation has limited emitting angle, and it is also absorbed differently by the X-ray emitting source, depending on the particular orientation. Alternatively, the detector moves and the X-ray unit repeatedly emits X-rays the entire region of examined teeth, which constitutes superfluous exposure to radiation.

In addition, X-ray generating unit must be exactly placed such that an affected part of the patient is appropriately imaged with a minimal dose of radiation. Such placing is difficult to perform.

U.S. Published Patent Application No. 2013/0010923 further discloses that when the electron source to X-ray source distance exceeds 3 cm, it is difficult to place the X-ray generating unit in the oral cavity, and electrons does not exactly reach the X-ray generating source, and thus a sufficient dose of X-ray radiation is not radiated, thereby deteriorating the quality of X-ray images obtained. Therefore, to achieve the miniaturization of the X-ray generating unit placed in the oral cavity, the X-ray generating source, the electron emitting source and a power connection unit are disposed on the same straight line axis, and when the elements are disposed on the same straight line, effects of a high voltage power line applied from the outside on the movement of electrons emitted from the electron emitting source are minimally exerted, thereby improving the stability of operating the X-ray generating device. However, making said alignment is also technically very difficult to perform.

An object of the invention is to provide solutions for the above concerns.

SUMMARY OF THE INVENTION

According to one aspect, an intraoral radiation device is provided, comprising a biocompatible intraoral receptacle with an X-ray source therein.

Some embodiments further comprise a power source operationally coupled to the X-ray source. The power source is enclosed within the receptacle in some embodiments.

In some embodiments the intraoral receptacle is configured to allow performing therewith bite-wing dental scans.

According to another aspect, an X-ray system for static intraoral radiation is provided, the system comprising:
  an intraoral X-ray device comprising an X-ray source;
  a dental X-ray system telescopic arm;
  an X-ray detector, and
  an X-ray detector mounting fixture configured to allow coupling the detector to the arm,
  the system configured to allow aiming the device and detector at each other.

According to yet another aspect, an X-ray system for panoramic intraoral radiation is provided, the system comprising:
  an intraoral X-ray source;
  a dental X-ray panoramic apparatus comprising:
  a frame;
  a stem held under the frame;
  head-rests and handles extending from the stem;
  a rotating arm having at least one extremity, the rotating arm being rotatable around said stem,
  an X-ray detector, and
  an X-ray detector mounting fixture configured to allow coupling
  the detector to an arm extremity,
wherein the system is configured to allow aiming the X-ray source and the detector at each other.

The X-ray device in any of these systems may be any of the devices described above.

The X-ray devices may further comprising a cover engageable with the intraoral receptacle,
  wherein the power source is rechargeable and comprises charger plugs, and the cover and intraoral receptacle are configured to allow exposing the charger plugs charging the battery when the cover is opened, and
  wherein when the cover is engaged with the intraoral receptacle, the X-ray source is water proof and electrically insulated.

The intraoral receptacle is preferably sterilizable; the intraoral receptacle and cover may also be sterilizable.

In some embodiments the intraoral receptacle is disposable; the cover and the intraoral receptacle may also be disposable.

According to another aspect, an X-ray system may comprise:
an X-ray device described above, and a rotating means operationally coupled to the X-ray source to allow rotation thereof. The rotating means is for example a MEMS device.

The X-ray system may further comprise a tracking device operationally coupled to the rotating means to control movement thereof.

The tracking device is for example an RFID.

In some embodiments, in the X-ray system:
the intraoral receptacle has an inner side;
  the X-ray source comprises an x-ray tube encapsulated within a housing;
  the housing is mounted on a hinge affixed to the inner side of the intraoral receptacle;
  wherein the rotating means allows the source to rotate on the hinge.

The rotating means may be encapsulated within the housing.

The X-ray system may further comprise a tracking device operationally coupled to the rotating means to control movement thereof, and
  wherein the tracking device is encapsulated within the housing.

In some embodiments, in the X-ray system:
the intraoral receptacle is hollow and has an inner side;
  the X-ray source comprises an x-ray tube encapsulated within a housing;
  the housing is mounted on a hinge affixed to the inner side of the intraoral receptacle;
  operationally coupled to the housing is a MEMS device, which allows generating a rotation of the source on the hinge;
  operationally coupled to the MEMS device is a passive RFID device,
  an active RFID device is mounted upon a rotating arm extremity, and
  the active RFID device is capable of controlling movement of the MEMS device via the passive device.

The X-ray system may further comprise:
  a MEMS device, which allows generating a rotation of the source;
  operationally coupled to the MEMS device is a passive RFID device;
  an active RFID device;
  wherein the active RFID device is capable of controlling movement of the MEMS device via the passive device, and the active device, the passive device and the detector have a common (spatial) frame-of-reference.

The X-ray source may comprise at least two separate electrical circuits, one of said circuits is a high-Voltage circuit, comprising two electrodes with high-Voltage therebetween, and the other circuit is an electron-source circuit which emits electrons when inserted into an electric field.

The high-Voltage source may comprise a high-Voltage capacitor; the high-Voltage source may further comprise a set of Voltage multipliers;

the X-ray source may comprise at least one PEC (Piezoelectric crystal).

In some X-ray device embodiments a first PEC is covered by a layer of a second PEC, wherein the first and second PEC have opposite polarizabilities. The first PEC may have a first width and the second PEC may have a second width, wherein the first width is larger than the second width.

According to another aspect, a kit comprising the device an inductive mat are provided, wherein the power source is provided with an induction coil, connected to a rectifier and to a DC charger, the inductive mat configured to allow charging the power source via the induction coil, rectifier and charger.

The x-ray source may comprise:
an enclosing vessel;
a first roller arranged at least partially within said enclosing vessel;
a second roller arranged at least partially within said enclosing vessel and arranged to be in rolling contact with said first roller; and
a drive assembly operatively connected to at least one of said first and second rollers,
wherein said drive assembly causes said first and second rollers to rotate while in contact to bring portions of said first and second rollers into and out of contact within said enclosing vessel as said first and second rollers rotate,
wherein said first roller has a surface at least partially of a first triboelectric material and said second roller has a surface at least partially of a second triboelectric material, said first triboelectric material having a negative triboelectric potential relative to said second triboelectric material,
wherein said enclosing vessel is structured to provide a controlled atmospheric environment, and
wherein said first triboelectric material, said second triboelectric material and said controlled atmospheric environment are selected such that rolling contact between said first and second rollers produces x-rays.

The first roller may have a rim with a tip and the second roller may have a groove matching the tip. The tip may have a width smaller than 50 μm.

The X-ray device and the X-ray detector may not be physically connected to each other. There may be no line-of-sight between X-ray device and the X-ray detector.

In some embodiments, the X-ray source further comprises means to accelerate and deflect electrons to an X-ray emitter, said means comprising:
an electron source;
a thin high-z anode, having a transmission geometry;
a set of deflection plates configured to allow a electron-beam from the electron source to be focused toward the anode.

The anode may have a surface area smaller than 100×100 μm².

The electron source may comprise a plurality of carbon nano-tubes.

BRIEF DESCRIPTION OF THE DRAWINGS

Some embodiments are herein described, by way of example only, with reference to the accompanying drawings. With specific reference now to the drawings in detail, it is stressed that the particulars shown are by way of example and for purposes of illustrative discussion of the preferred embodiments only, and are presented in the cause of providing what is believed to be the most useful and readily understood description of the principles and conceptual aspects of the invention. In this regard, no attempt is made to show structural details in more detail than is necessary for a fundamental understanding of the invention, the description taken with the drawings making apparent to those skilled in the art how the several forms may be embodied in practice.

The following figures provide some more details about some methods used in some embodiments.

GLOSSARY

Bitewing: a dental X-ray film designed to show the crowns of the upper and lower teeth simultaneously MEMS: Microelectromechanical systems Periapical: related to the tissues surrounding the apex of the root of a tooth RFID: Radio-frequency identification systems are wireless non-contact systems that use radio-frequency electromagnetic fields to transfer data from a tag attached to an object, for the purposes of automatic identification and tracking.

DETAILED DESCRIPTION OF THE INVENTION

Figure 1A:
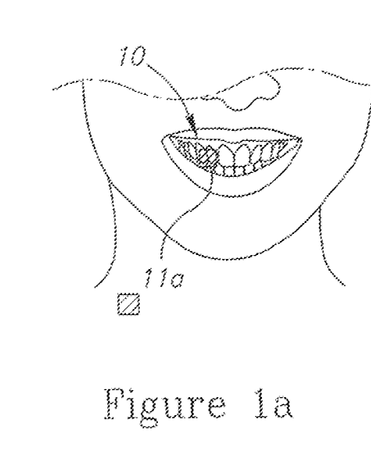
FIG. 1a schematically shows bitewing geometry.
Figure 1B:
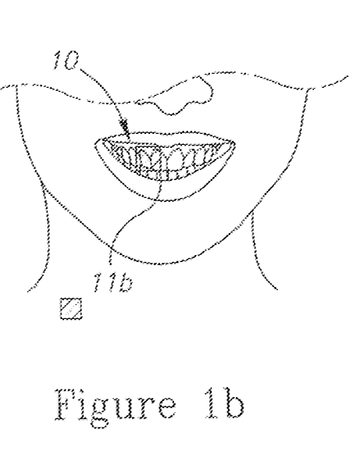
FIG. 1b schematically shows a periapical geometry.
Figure 1C:
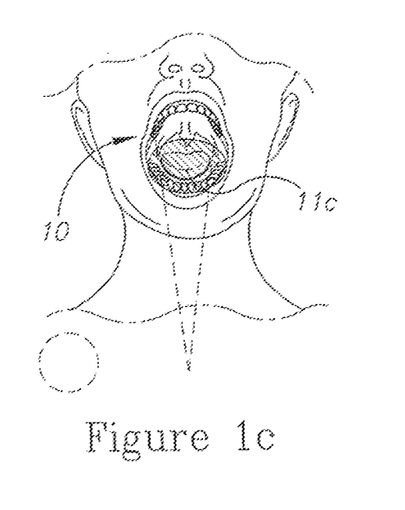
FIG. 1c schematically shows a palatal geometry.

The embodiments described herein below provide solutions for the above described concerns, FIGS. 1a, 1b and 1c schematically show bitewing geometry, periapical geometry and palatal geometry, respectively, wherein the scan in the mouth 10 is of areas 12a, 12b and 12c, respectively.

Figure 2A:
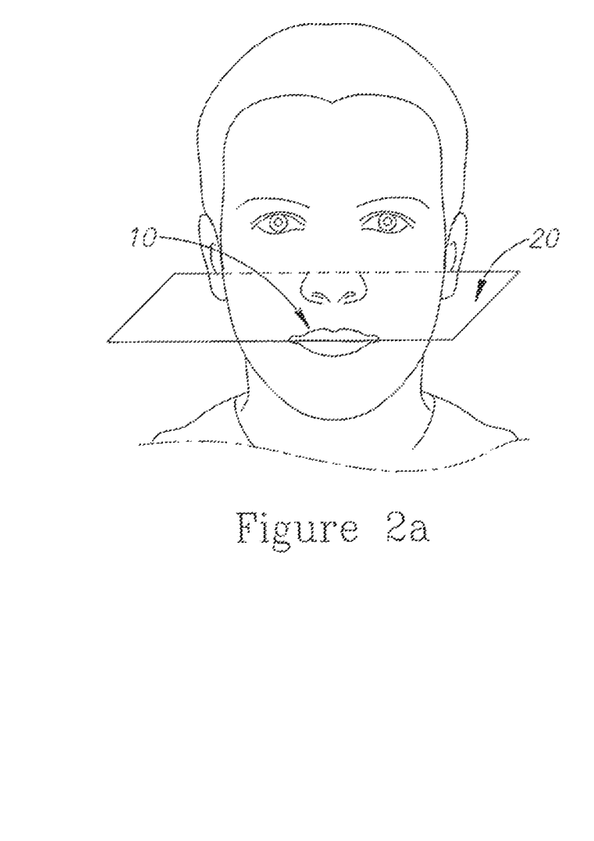
FIG. 2a schematically shows the occlusal plane.

FIG. 2a schematically shows the occlusal plane 20 and

Figure 2B:
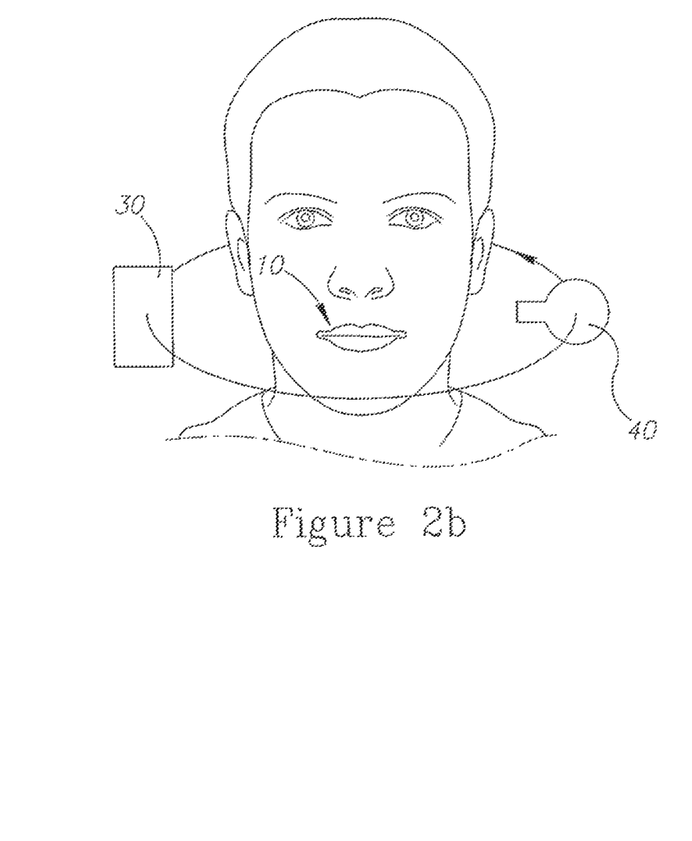
FIG. 2b schematically shows a prior art panoramic scan with an FPD) and an X-ray tube outside the mouth.

FIG. 2b schematically shows a prior art panoramic scan with an FPD 30 and an X-ray tube 40 outside the mouth 10.

In the most common X-ray systems a static imaging is taken by a patient holding with his teeth a detector placed in his mouth. For example, for the palatal imaging, an FPD is tilted to the occlusal plane, above or below it. A dental X-ray system telescopic arm equipped with the X-ray source is brought close to the detector. The telescopic arm provides all the required degrees-of-freedom to bring the X-ray source to the desired position.

According to one aspect, the positions of the X-ray source and the detector (FPD, etc.) are now exchanged from their respective traditional positions: The source is firmly positioned inside the patient mouth, whereas the FPD is now mounted on said arm. In preferred embodiments the source is rotatable to allow the source to face the detector. An FPD mounting fixture may be all that is required to adapt the arm for these embodiments.

According to one aspect, in the static imaging, the FPD is mounted far (at least 10 cm) from the patient's head, such that the resolution is set by the X-ray beam's spot size (typically 30 µm). The FPD is moved to face the ROIs, preferably followed by the tube head.

Figure 3:
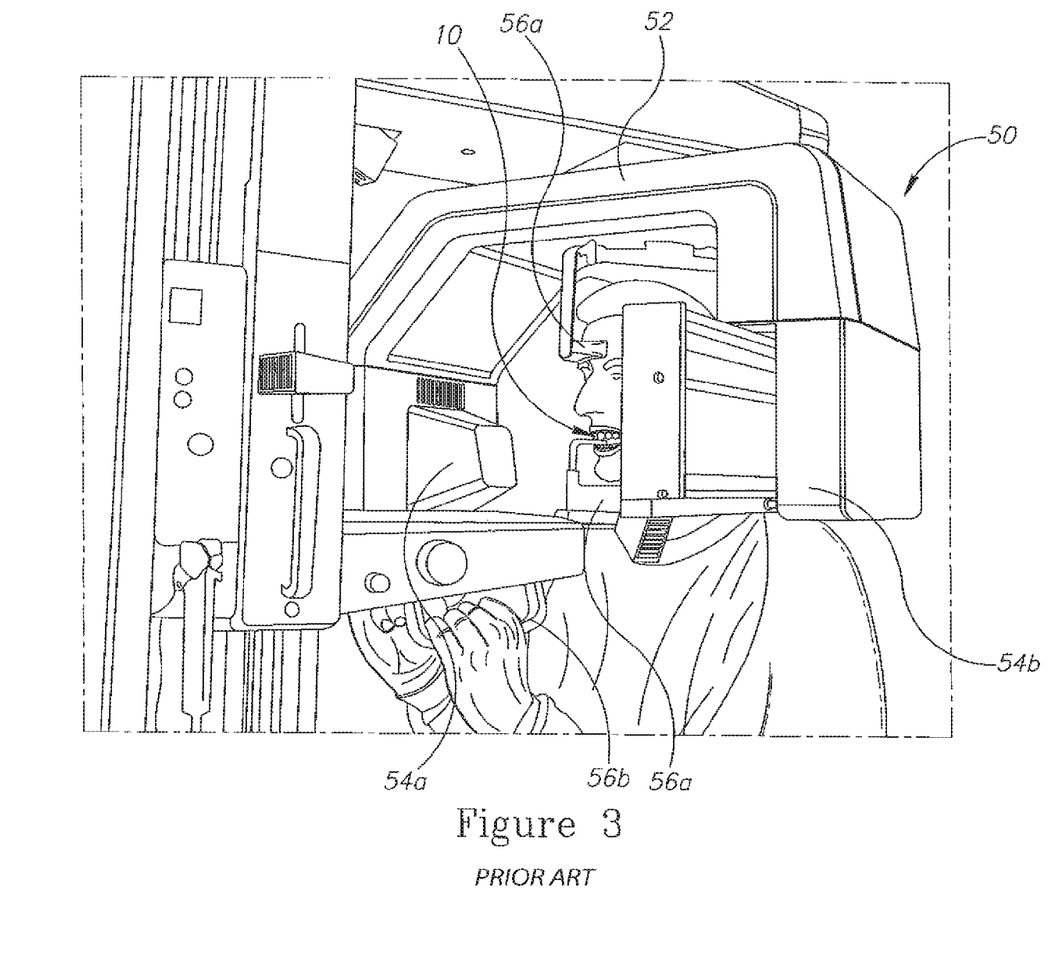
FIG. 3 shows a prior art dental panoramic radiography system, comprising a horizontal rotating arm which holds an X-ray source and detection means arranged at opposed extremities respectively, and head-rests and handles extending from a stem (not shown) held under the frame of the system. The rotating arm is rotatable around said stem.

FIG. 3 shows a prior art dental panoramic radiography system 50, comprising a horizontal rotating arm 52 which holds an X-ray source and detection means arranged at opposed extremities 54a, 54b, respectively, and head-rests 56a and handles 56b extending from a stem (not shown) held under the frame of the system 50. The rotating arm 52 is rotatable around said stem.

In the bitewing and in the periapical geometries, the FPD has to be mounted close to the occlusal (central) plane. Therefore, in some panoramic radiography embodiments, as well as some embodiments for radiography in the bitewing and in the periapical geometries, the panoramic mounting arm of commercially available panoramic dental X-ray systems can be used, whose plane-of-rotation can be arranged to collide with the occlusal plane.

According to one aspect, a commercially available panoramic system is adapted, and a panoramic scan is performed as follows: the patient's head is positioned on head-rests while the FPD continuously rotates around the patient's head. X-ray photons are emitted by the intraoral x-ray tube, whose head tracks the moving FPD. Finally, the image is reconstructed as known in the art.

Figure 4:
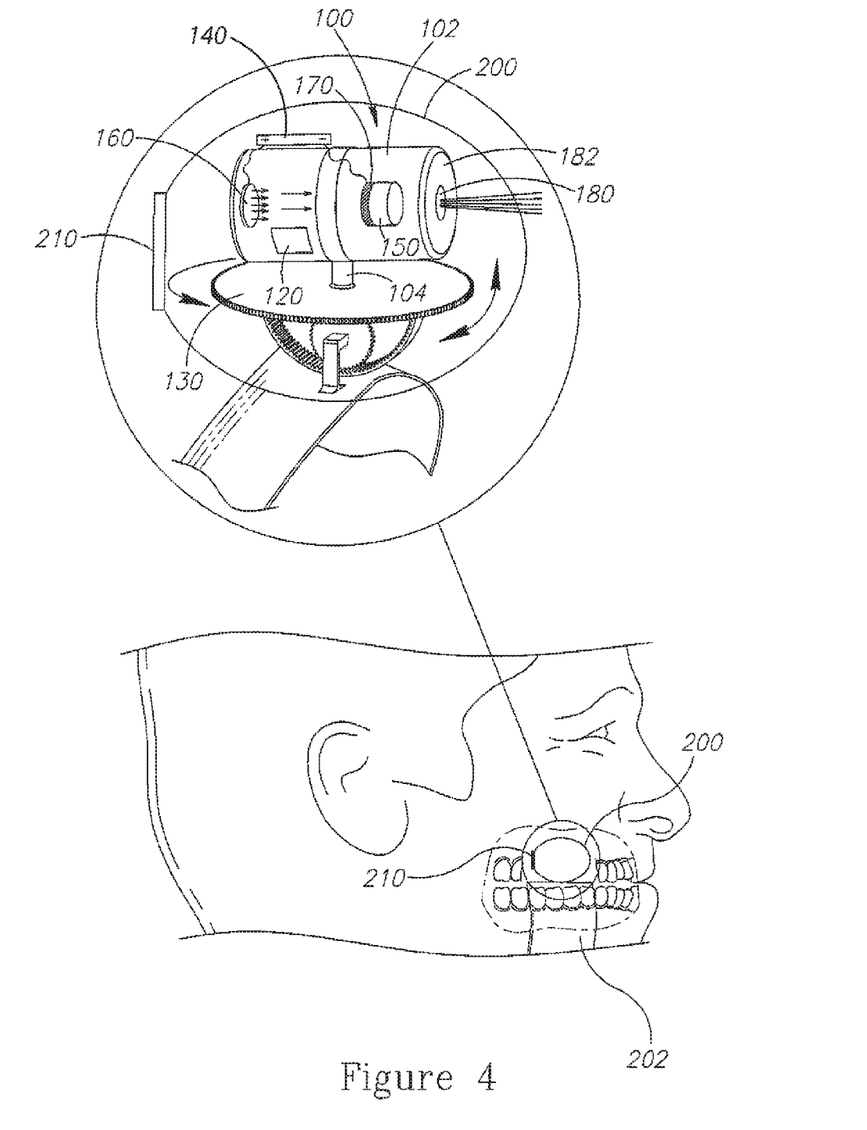
FIG. 4 depicts an apparatus for intraoral x-ray imaging, in which the X-ray source comprises a miniature x-ray tube encapsulated within a cylindrical housing. Said housing is mounted on a hinge affixed to an inner side of an intraoral biocompatible intraoral receptacle. Operationally coupled to said cylindrical housing is a RFID device, which controls the source orientation in space, and a MEMS device, which generates the required rotation of the source on hinge 104 to the correct orientation. The source is energized by a power source, also mounted within the intraoral receptacle.
Figure 5:
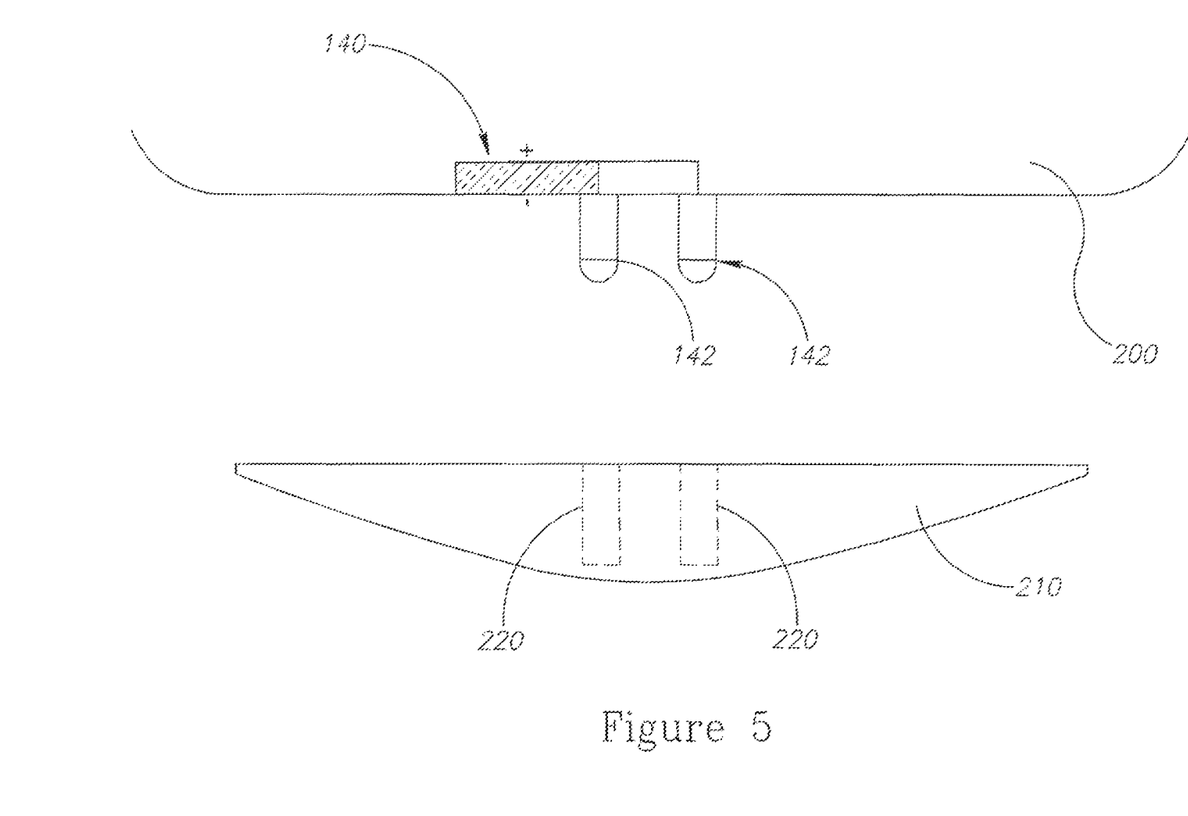
FIG. 5 illustrates an exemplary article shaped as a female socket, covering charger plugs when in the intraoral positioning. The cover is configured to allow sealing the interior of the intraoral receptacle from the environment and when uncovered, the charger plugs can be plugged into a DC charger for recharging.

According to one aspect, as schematically shown in FIG. 4, an apparatus for intraoral x-ray imaging is mounted on bite-block 202, in which the X-ray emitting device 100 comprises a miniature x-ray tube (electron source 160, tube anode 170, and heat sink 150) encapsulated within a cylindrical housing 102. Said housing 102 is mounted on a hinge 104 affixed to an inner side of an intraoral biocompatible intraoral receptacle 200 (comparable to commercially available bite-blocks) covered with a cover 210. Operationally coupled to said cylindrical housing 102 is a tracking device, for example, a RFID device 120, which controls the emitting device 100 orientation in space, and a rotator for generating a rotation of the emitting device 100, for example, a MEMS device 130, which generates the required rotation of the emitting device 100 on hinge 104 to the correct orientation. The emitting device 100 is energized by a power source (for example, rechargeable battery) 140, also mounted within the intraoral receptacle 200. The intraoral receptacle 200 may be non-toxic, preferably biocompatible, and may be disposable or sterilizable (for example, by autoclave), or in other embodiments is covered by a bio-compatible sheet (not shown) that is similarly disposable or sterilizable. As shown in FIG. 5, a cover 210, part of this disposable sheet, or of the receptacle 200, or a separate article, is shaped as a female socket 220, covering the charger plugs 142 when in the intraoral positioning. The cover 210 is configured to allow sealing the interior of the intraoral receptacle 200 from the environment, i.e., the interior is both electrically insulated and waterproof. When uncovered, the charger plugs 142 can be plugged into a DC charger for recharging.

In some embodiments the power source is charged by wireless charging, which has gained much attention recently (http://en.wikipedia.org/wiki/Inductive_charging). An inductive mat is provided, and each tube head is provided with induction coil, connected to a rectifier and to a DC charger. A similar charging structure is manufactured by Witricity, http://en.wikipedia.org/wiki/WiTricity.

Returning to FIG. 4, further schematically shown within the emitting device 100 are high Voltage source 140, a tube anode 170 (for producing the X-rays), and an X-ray window 180 shielded with an x-ray shield 182, whose roles are well known in the art.

The intraoral receptacle has dimensions allowing the source to be intraorally positioned.

In some embodiments, sets of intraoral sources are provided. For example, three different sizes can be used, one for pediatric and two for adult sizes. Separate source sets may be provided, one for Bitewing and Periapical scans, and the other for Palatal scans. The former may be encapsulated inside a flattened ellipsoid, whose dimensions, for an adult patient, may be about 2.5 cm in diameter and 1.5 cm height, for example between 2 and 3 cm, and 1 and 2 cm, respectively, for example. When the receptacle is inserted, the ellipsoidal intraoral receptacle depresses the patient's tongue, thus allowing exposure of both upper and lower teeth. For the Palatal scan, the receptacle may be more elongated, about 3 cm in length and 1.5 cm in diameter, for example, between 2.5 and 3.5 cm, and between 1 and 2 cm, respectively, and mounted vertically inside the mouth. For imaging the upper jaw, the ellipsoid head, whereabout the X-ray window is situated, is pressed up with the tongue, to the palate. Similarly, for imaging the lower jaw the ellipsoid is reversed in orientation and it is pressed down (pressing the tongue to the mandible center), for complete capturing of the maxilla.

In some embodiments the rotating means is also capable of moving the source up and down to a limited extent (see small arrow in the figure) for the purpose of fine adjustment of the source's position.

Figure 6:
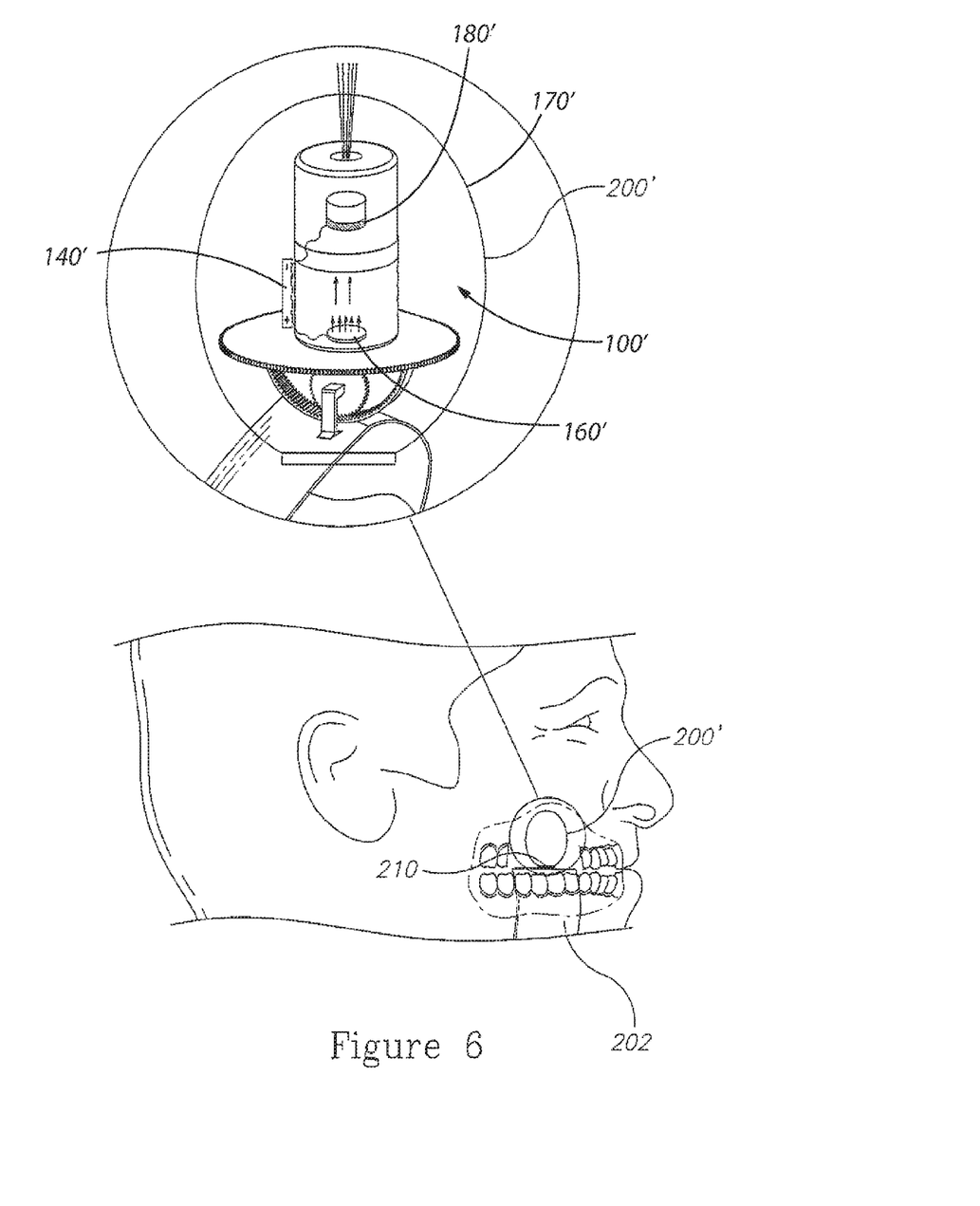
FIG. 6 shows an X-ray emitting device wherein the source is situated in a suitably sized and shaped intraoral receptacle, oriented so that the window is proximal to the upper teeth.

FIG. 6 shows an X-ray emitting device 100' wherein a miniature x-ray tube is situated in a suitably sized and shaped intraoral receptacle 200', oriented so that, as mentioned above, the anode 170' and the window 180' are proximal to the upper teeth. The voltage source 140' and the source of the exciting electrons 160', are thus distal to the upper teeth.

In some embodiments the rotating means is also capable of moving the source in a horizontal plane to a limited extent (see small arrow in the figure) for the purpose of fine adjustment of the source's position.

Some embodiments comprise an FPD that is configured to allow both panoramic and static imaging. The high resolution required for static imaging is achieved by using an x-ray tube with a small focal spot and by keeping the FPD farther away from the patient's mouth. For example, for a spot-size of 30 µm, the window of the intraoral source is positioned at a distance of 1 cm from the tooth, and with a detector having an FPD pixel-size of 100 µm, and located at a distance of 10 cm from the tooth, the resulting resolution is 28.8 µm, close to the desired 30 µm.

Some embodiments comprise a small x-ray tube with a low heat capacity as the intraoral geometry brings the tube much closer to the tooth than in the standard geometry. Using the above example, if intraoral distance of the X-ray tube from the tooth is 1 cm, and if the standard extra-oral distance is 25 cm, then the required x-ray output of the intraoral device is 625 $(=(25/1)^2)$ times smaller than the output of extra-oral tubes. If a typical tube current is 12.5 mA in the extra-oral geometry, then about 20 µA $(=12,500/625)$ suffices for the intraoral embodiments. Compare to the 1-15 mA current or higher that is required when using the prior art systems.

The tube may comprise deflection plates which help to focus the X-ray beam, without appreciable loss of intensity of the beam.

The proximity of the tube to the target affords a much larger acceptance angle than in commercially available systems, resulting a much faster scan and greater tube efficiency.

In some embodiments the system is configured to allow the same FPD mounting-arm to be used both for panoramic and for Bitewing and Periapical imaging. The panoramic FPD is rotated to the desired position, and exposure is made with x-ray emanating from the intraoral source, without using the built-in extra-oral source. Furthermore, if a sequence of static images is required, then the system can be programmed to shift the FPD to preset positions and to take exposures there, without the need for dentist intervention.

Some embodiments comprise remote-sensing devices, RFID systems for instance, for the purpose of automatically orienting the head of the intraoral tube toward the external FPD. In some embodiments, an active RFID tag is mounted upon a rotating arm extremity, for example on the FPD, and a passive tag is mounted on the tube head, which keeps tracking after the active FPD center. The active tag may include a transceiver antenna, analog detection circuits, CPU for computations and MEMS remote control. Upon operation, the antenna sends an RF signal, senses the passive-tag's coil and detects its orientation. Then the active tag controls the source MEMS to rotate the tube head to the required orientation.

Figure 7:
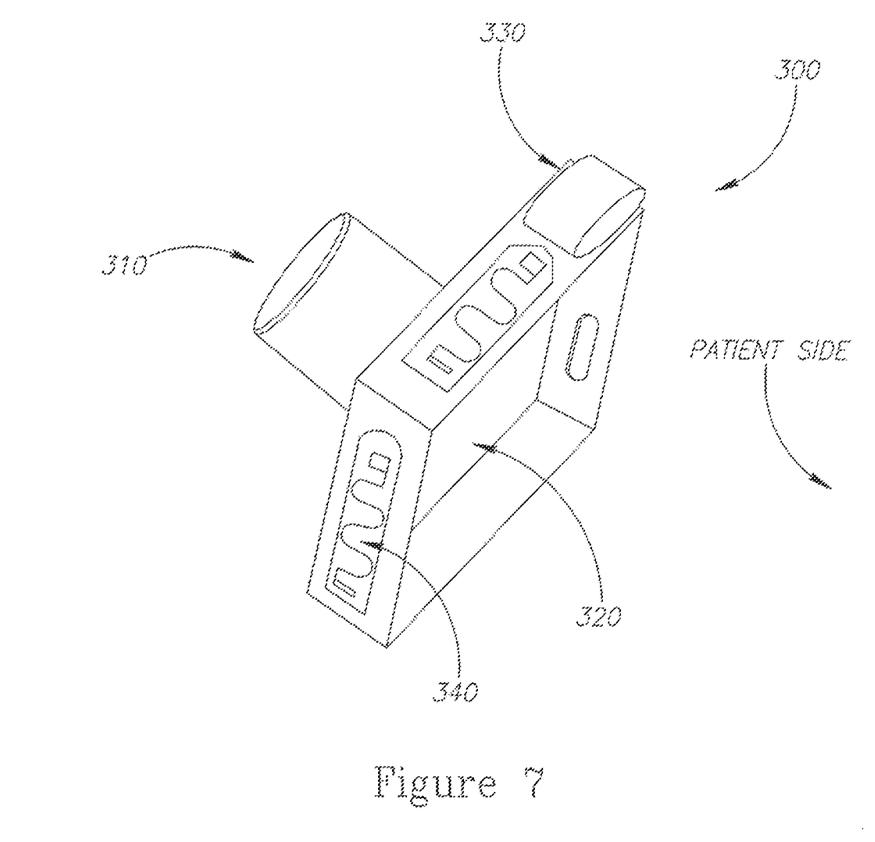
FIG. 7 schematically shows one an embodiment wherein the X-ray system has the active device, the passive device and the detector with a common (spatial) frame-of-reference (FOR): with an adaptor (for adaptation of the tag to telescopic or panoramic arm), a housing, and RFID reader and reference RFID tags therein or thereon.

Thus, some X-ray system embodiments have the active device, the passive device and the detector with a common (spatial) frame-of-reference (FOR). FIG. 7 schematically shows one such embodiment 300 with an adaptor 310 (for adaptation of the tag to telescopic or panoramic arm), a housing 320, and RFID reader 330 and reference RFID tags 340 therein or thereon.

A common FOR of two objects is achieved by accurate measuring the spatial- and angular-displacements between the two objects. A common FOR of the RFID reader 330 and the center of the FPD (not shown) is achieved by means of two or more reference RFID tags 340, which are affixed to the FPD or to its housing 320. Once the RFID reader senses the positions and orientation of the reference tags, the 3D coordinates of the FPD center are evaluated. Then, when the passive tag is intraorally inserted, the RFID reader senses its position and orientation, and relates it to the already-known coordinates of the FPD center. Having such FOR is an advantage as separate positioning of each component is not required.

According to another aspect, a set of sources is provided, suitable for use by a clinic for selection of a system, with a variety of characteristics: intraoral receptacle size, tube-head positioning, spot size, tube material, battery capacity, etc. Furthermore, a multi-battery charger is provided in some embodiments, wherein a plurality of sources can be charged in parallel. The dentist can then choose the appropriate source, in accordance with the required scan (static/panoramic, bitewing/palatal, patient size, required detailing) and return it for recharging after the scan, having another source ready for the next patient.

In certain embodiments, the x-ray tube may comprise high-Voltage sources and a field-emission electron source made, for instance, out of a Carbon Nano Tube (CNT). An essential feature of this embodiment is the separation between two electrical circuits: the high-Voltage circuit and the electron-source circuit. The high-Voltage circuit provides the accelerating Voltage. It might comprise a high-Voltage capacitor, charged to the desired kV, or, alternatively, it might comprise a Pyroelectric crystal (PEC) which is activated by means of heating/cooling cycle (see details below). Said high-Voltage circuit does not store a large amount of electric energy. Therefore, it can be made small enough to be a part of the intraoral tube. For example, the size of 10 nF high-Voltage capacitors can be about 1 cm height and 1 cm outer diameter. The PEC can be a rectangle of 3 mm·5 mm·5 mm.

The required energy is provided by the electron source circuit. However, this circuit utilizes a relatively low Voltage (typically 100-500V) and is therefore much easier to adapt and to integrate.

The electrons are emitted by the electron-source and are accelerated by the high-Voltage to a thin layer of high-Z anode material (e.g., Molybdenum) attached to low-Z heat-sink block (e.g., beryllium block). All of the above are mounted inside a sealed high-vacuum tube. The tube is enclosed within a cylinder of high-z material (e.g., lead) that has a thin beryllium window, either in a front-panel of the cylinder (for bitewing and panoramic geometry) or surrounding the cylinder, near its edge (for palatal geometry). In some embodiments, however, the same tube can be mounted either horizontally (for bitewing and panoramic geometry) or vertically (for palatal geometry) inside the intraoral receptacle.

As explained above, some high-voltage embodiments comprise pyroelectric crystals (PEC). These crystals have a very large spontaneous polarizibilty. At room temperature, surface-adsorbed electrical charges mask the intrinsic field. However, when the crystal is heated, the intrinsic field is revealed, which can be as large as a few hundred thousand Volts, depending on the sample crystal size and on the crystal characteristics (polarizibilty, breakdown voltage). Therefore, when heated, the pyroelectric crystal can serve as a high-voltage generator.

For example, the technology described in U.S. Pat. No. 7,741,615 is a simple arrangement of the x-ray source may be based upon PZC (Piezoelectric crystals), which has a needle-shaped tip. The back of the PZC is electrically connected to high-Z electrode (anode), and both the PZC and anode are mounted in vacuum within a sealed tube. When the PZC is heated, a large electric field is applied between the tip and the anode, which reaps electrons from the tip and accelerates them to the electrode. X-rays are produced when the electrons are stopped by the anode. A similar approach is used by a commercial vendor for various on-the-shelf designs (http://www.amnptek.com).

EP2418671 describes a more sophisticated arrangement, ultraviolet light irradiates a small portion of the PEC. The light heats the PEC portion and also directly causes emission of electrons from the PEC surface; the electrons are then accelerated to a nearby high-Z anode.

A preferred method of using PECs at present is described by Aronov and Rosenman (Aronov D, Rosenman G. "Surface Energy Modification by Electron Beam", Surface Science, 601 5042 (2007). The method uses PECs for providing a required large voltage drop, but not for supplying the electric charge. A wide PEC (designated "the first", below) is covered by a thin layer of another PEC ("the second"), which has an inverse polarizability. When heated, a large electric field is produced across the first PEC. A smaller electric field is applied across the second PEC, which is also reversed in its polarity. Thus, the second PEC acts as "anti-emitter" which repels the electrons from the first PEC's surface. This solves the problem of surface-discharge, typical to PECs at high voltages, so the produced high-Voltage is more stable and the PECs maintain their high surface quality for a much longer time. Evidently, the PECs don't supply the electrons. The electrons are emitted by a different source (possibly CNT, as described above) which is mounted between the two PECS and the grounded anode.

Alternatively, the high-Voltage source comprises a high-Voltage capacitor. Such capacitors are commercially available (e.g., by "General Atomics" http://www.ga-esi.com/). The size of the capacitor depends on its capacitance, and capacitors of <10 nF can be built as a cylinder with 1 cm height and 1 cm outer diameter. This high-Voltage capacitor may be charged to the high Voltage (60 kVp) externally and then inserted into the patient mouth. Alternatively, it can be charged at a lower Voltage (about 2 kVp) and then connected to a set of Voltage-multipliers, for increasing the Voltage to the desired high Voltage.

In alternative embodiments, the x-ray tubes may be structured to allow the triboclectric effect to occur in the source.

The key features of such sources are:

No high-Voltage is required, and high voltage is performed by the inherent charge separation; only moderate vacuum (~1 mTorr) is required in the tube; and focal spot size is set by the size of the contact point.

Such embodiments particularly lend to miniaturization of the X-ray source, as no external high-Voltage supply and no high-vacuum levels are required.

In triboelectricity, electrostatic generators store integrated charge that is developed when two materials are rubbed together in frictional contact. The materials are selected to be furthest apart in the triboelectric series—an empirically derived list showing both the propensity of the materials to charge and the polarity of charge (P. E. Shaw, Proc. R. Soc. Lond. A94, 16 (1917)). At the point of contact between the two materials, the frictional electrification may be of such magnitude that it may ionize the gas surrounding it, creating triboluminescence. Triboluminescence is observed for example during peeling pressure sensitive adhesive (PSA) tape and has an electrostatic origin: When the tape is peeled, charge densities are exposed on the surfaces of the freshly peeled region and subsequently discharge (C. G. Camara, J. V. Escobar, J. R. Hird and S. P. Putterman, Nature 455, 1089 (2008)). If the tape is peeled in vacuum, it has been found that the triboluminescence produced extends to X-ray energies (V. V. Karasev, N. A. Krotova and B. W. Deryagin, Dokl. Akad. Nauk. SSR 88 777 (1953)). It has been found that the X-ray discharge from peeling tape was sufficiently self-collimated at the peel line to resolve the inter-phlangeal spacing of a human digit. The emission of nanosecond X-ray pulses allowed an estimate of the emission region to be calculated. Subsequent research on peeling PSA tape with a width of 1.5 mm has confirmed that the process takes place at dimensions less than 300 μm (C. G. Camara, J. V. Escobar, J. R. Hird and S. P. Putterman, Appl. Phys. B 99, 613 (2010)).

For the most effective charging to occur, intimate contact between the materials and cleanliness of the contacting surfaces is important (R. Budakian, K. Weninger, R. A. Hiller and S. P. Putterman, Nature 391, 266 (1998)).

Figure 8:
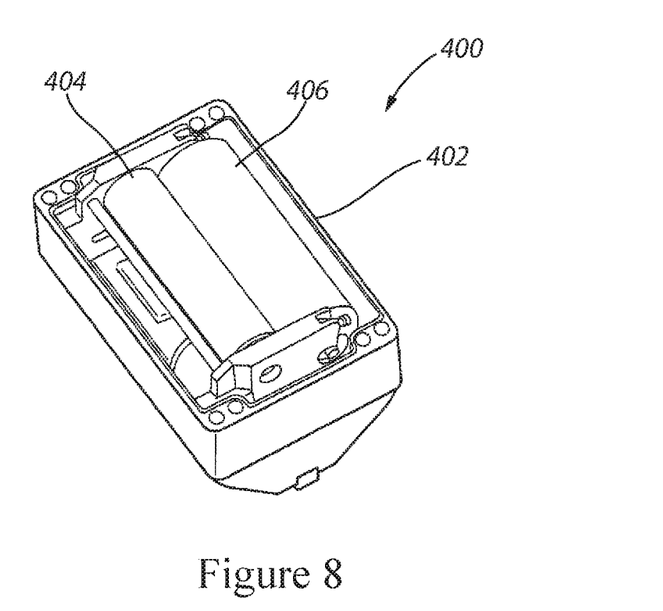
FIG. 8 is a schematic illustration of a triboelectric x-ray source according to an embodiment, shown in a partially assembled view to allow internal structure to be viewed. The x-ray source includes an enclosing vessel; a first roller arranged at least partially within the enclosing vessel; a second roller arranged at least partially within the enclosing vessel and to be in rolling contact with the first roller.
Figure 9:
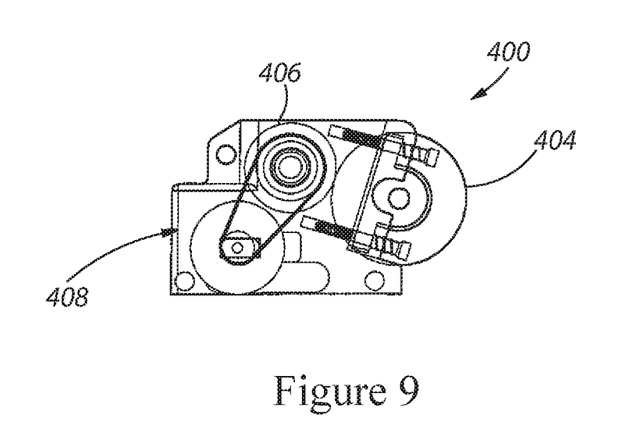
FIG. 9 shows a drive assembly in the X-ray source shown in FIG. 8.
Figure 10:
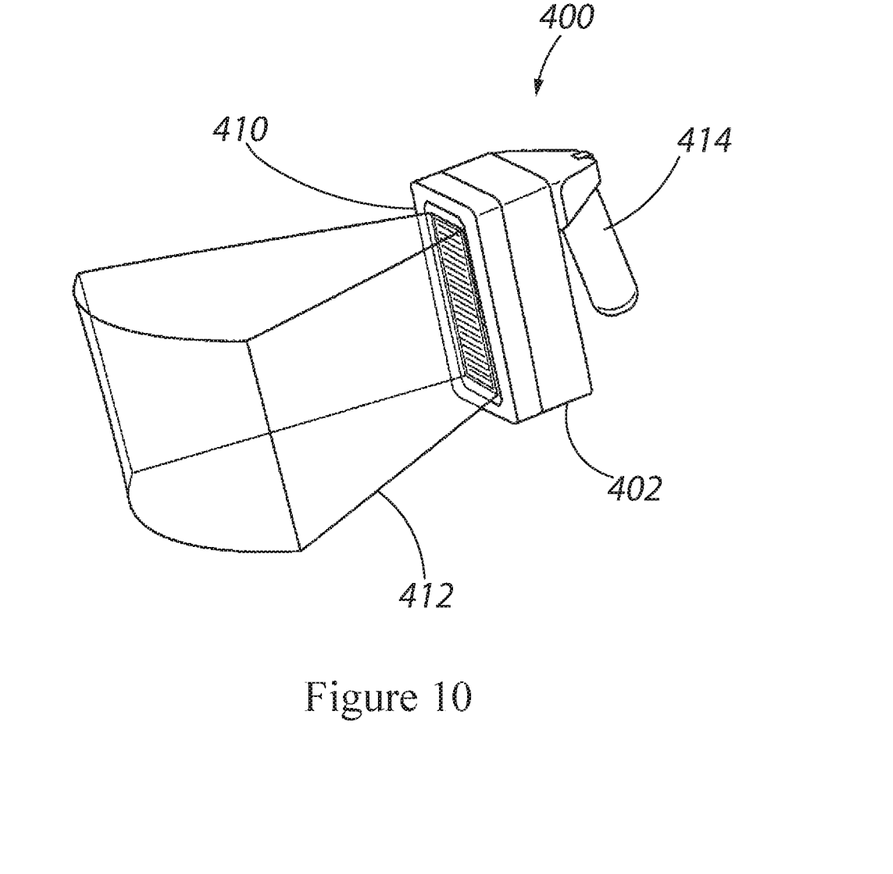
FIG. 10, shows a triboelectric source in which the enclosing vessel of the x-ray source has an x-ray window that is substantially transparent to x-rays relative to remaining portions of the enclosing vessel. In other words, the enclosing vessel provides shielding to substantially block x-rays from exiting the vessel except through the window. The enclosing vessel, including the window, maintains a vacuum such that a gas pressure within the vessel is less than the atmospheric pressure immediately outside the vessel.

FIGS. 8-10 show illustrations of an exemplary triboelectric X-ray source 400 for generating X-rays with at least one according to an embodiment.

FIG. 8 is a schematic illustration of an x-ray source 400 according to an embodiment. The x-ray source 400 in FIG. 8 is shown in a partially assembled view to allow internal structure to be viewed. The x-ray source 400 includes an enclosing vessel 402; a first roller 404 arranged at least partially within the enclosing vessel 402; a second roller 406 arranged at least partially within the enclosing vessel 402 and to be in rolling contact with the first roller 404; and a drive assembly 408 (FIG. 9) operatively connected to at least one of the first roller 404 and second roller 406.

The drive assembly 408 causes the first and second rollers 404, 406 to rotate while in contact to bring portions of the first and second rollers 404, 406 into and out of contact within the enclosing vessel 402 as the first and second rollers 404, 406 rotate. The first roller 404 has a surface at least partially of a first triboelectric material and the second roller 406 has a surface at least partially of a second triboelectric material. The first triboelectric material has a negative triboelectric potential relative to the second triboelectric material. The order of the materials can be reversed in other embodiments. The enclosing vessel 402 is structured to provide a controlled atmospheric environment. The first triboelectric material, the second triboelectric material and the controlled atmospheric environment are selected such that rolling contact between the first and second rollers 404, 406 produces x-rays.

Referring to FIG. 10, the enclosing vessel 402 of the x-ray source 400 has an x-ray window 410 that is substantially transparent to do x-rays 412 relative to remaining portions of the enclosing vessel 402. In other words, the enclosing vessel 402 provides shielding to substantially block x-rays from exiting the vessel 402 except through the window 410. The enclosing vessel, including the window 410, maintains a vacuum such that a gas pressure within the vessel 402 is less than the atmospheric pressure immediately outside the vessel 402. In an embodiment, the enclosing vessel 402 is constructed to maintain a pressure less than $10^{-1}$ torr. In an embodiment, the enclosing vessel 102 is constructed to maintain a pressure greater than $10^{-9}$ torr and less than $10^{-3}$ torr.

In another embodiment, at least one of the first roller 404 and the second roller 406 has at least two surface regions of different triboelectric materials such that at least two different x-ray spectra are produced during rolling contact between the first and second rollers 404, 406. As one should readily recognize, various embodiments can include rollers coated with one, two, three or more types of triboelectric materials, which could also be coated in selected spatial patterns, to alter the type of x-ray spectrum produced by the x-ray source 400. In addition, materials that include one or more selected atomic elements that have desired excited states to enhance narrow band x-ray emission can also be included.

Batteries or other electrical storage means could be located in the handle 414. In some embodiments, the x-ray source 400 can further include a photovoltaic element. In further embodiments, the x-ray source 400 can also include a hand-operated charger. In some embodiments, the drive assembly can include a hand-operated mechanism (not shown in the drawings). This can include a hand crank, for example. Such a hand-operated mechanism can be either in place of, or in addition to, an electric motor.

X-ray pulses can be generated when the pressure is lower than $10^{-3}$ torr and the contacting materials are a metal vs. a polymer insulator. Also, a contact area of about 1 mm² has been found suitable for producing x-ray pulses. The x-ray pulses can be on the order of tens of nanoseconds, for example.

Further details about the structure and operation of various triboelectric sources may be found in WO2012125492, WO2009102784 and WO2012154494, each of which is incorporated herein by reference.

The relevant technologies for the X-ray source can therefore be divided into two families: (1) Triboelectric-based and (2) Regular generator-tube setup. Table 1 summarizes the principles behind the two technologies:

TABLE 1

| Technology/ Parameter | Triboelectric | Generator-tube |
| --- | --- | --- |
| High Voltage generator | Charge separation | High-Voltage capacitor or PEC crystal |
| Electron source (cathode) | Adhesive charge on the negatively-charged wheel | Carbon nanotubes |
| Anode | The positively-charged wheel | High-z plate, potentially attached to a low-z block, for heat dissipation |
| Design constraints | Low Vacuum: ~1 mTorr; Wheel materials must be rigid enough to sustain long-life friction | High Vacuum: ~$10^{-8}$ Torr, might require perpetual degassing Deflection plates might be required |

The main technical parameters of each technology are:

Triboelectric Assembly:

Voltages up to 60 kVp have been obtained. Higher Voltages (>70 kVp) are expected to be attained upon using different materials/compositions, without substantially changing the geometry.

Charge densities of $10^{12} e^-/cm^2$ are typical. An X-ray flux of $10^8 \gamma/sec$ is measured, which is sufficient for the intraoral application.

Figure 11A:
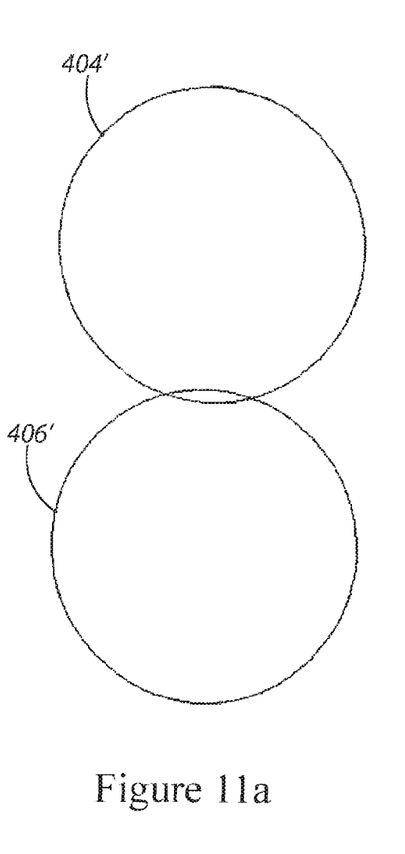
FIG. 11a schematically exhibits triboelectric rollers in a side-view for use in some embodiments.
Figure 11B:
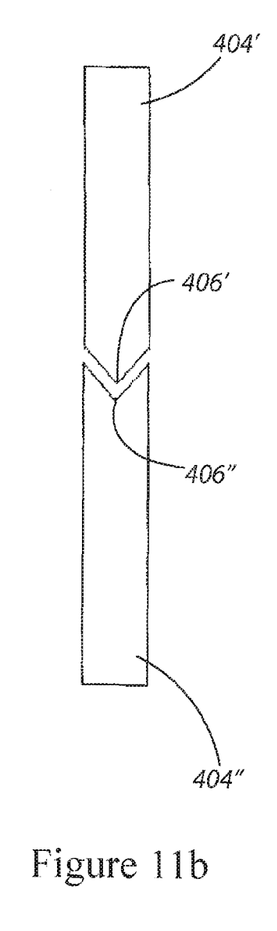
FIG. 11b shows the same rollers in a frontal view.
Figure 11C:
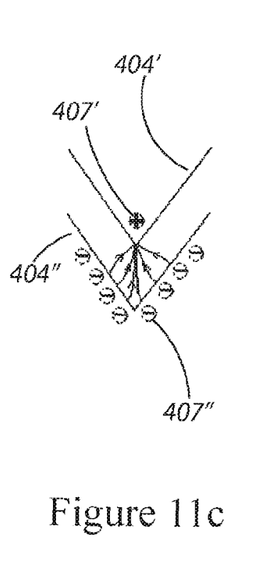
FIG. 11c shows the same rollers in top view.

Using the rollers described above, the spot size depends on the overlap area between the two rollers. If the overlap is designed as in FIGS. 11 a-c (exhibiting the wheels in a side-view, frontal view and top view, respectively), i.e., the rim of a first roller 404' has a tip 406' of width less than 50 μm and the second roller 404" has an essentially matching groove 406" then, when the rollers are rotated, the negative charges 407" are attracted to the sharp tip 406'. When the X-rays are collected in normal viewing angle (i.e. out-of-the page in FIG. 11c), the resulting apparent X-ray source is as small as 50 μm-50 μm.

Using current MEMS technology, the intraoral radiation device, comprising the X-ray source and a power source operationally coupled to the X-ray source, can be packed in a space as small as 5·5·10 mm.

Generator-Tube Assembly:

High-Voltage capacitors (with up to 100 kV) can be found commercially (see e.g. http://www.ga-esi.com/)). Capacitor size can be small (<1 cm) if capacitance is small (<10 nF, for example). As explained above, the high-Voltage source is not the source of the electrical current. Therefore, it should not store large amounts of electrical charge. Therefore, 10 nF suffice for proper operation of the X-ray source.

Pyroelectric devices can provide up to 100 kV. Commercially available miniature HV suppliers can provide voltages up to 2 kV (http://www.ahv.com/events.php?vf_id_event=14).

Currents depend on the CNT preparation and on tube geometry. Currents of 5 mA (two orders of magnitude higher than required for the intraoral embodiments described above) were obtained in demo setup (http://iopscience.iop.org/0957-4484/20/32/325707/pdf/0957-4484_20_32_325707.pdf—"Calderon-Colon").

CNT tips are 1-10 nm in diameter. Such tips can be grown in arrays with less than 2 μm between adjacent tips (Calderon-Colon). Therefore, the CNT can provide the required high-resolution, and the size of the source depends on the uniformity of the field-emission electric field. Electrodes as small as 10 nm can be produced (http://www.xintek.com/products/cathodes/point.htm). A focal spot of 100 μm·100 μm in size was produced and tested (Calderon-Colon).

A high vacuum is required for avoiding arcing of gasses in the tube. Vacuum of $~10^{-8}$ Torr can be held for long time, if a small current is constantly held in the tube (the electrons ionize the gas molecules and cause them to accelerate and to be adsorbed to the electrodes). Under such Vacuum, a tube of ~1 cm long can hold 70 kVp without arcing.

To summarize, the embodiments described above provide one or more of the following advantages:

a) The entire x-ray source is truly intraoral (no cables to the outside world);

b) Rotation of the source is by intraoral MEMS, without needing to resort to external shafts etc.;

c) Mutual orientation of the intraoral source and external detector is achieved by means of RFID, thus no line-of-sights (power source-electron source-radiation source) is required and the device allows imaging requiring the patients to have their teeth pressed together;

d) Provision of a source having a small focal-spot size, typically around 30 μm wide. The small spot allows using the clinic FPD (with lower resolution) even for imaging that requires film-like resolution;

e) Being much closer to the object than in the standard geometry, a much smaller tube current is required, typically about 20 μA. Therefore, even a small tube design can provide the required technique and power;

f) The source may work in forward (transmission) or in backward (reflection) geometry. In both cases the angular opening is limited to, say, 30°-40°, such that the radiation is relatively uniform. Therefore, no additional moveable collimator is required, and g) System-wise: the system allows upgrading existing dental-clinic setups for operation embodiment: existing panoramic apparatus can be used both for panoramic scan and for status scans. The existing x-ray-tube mount (that every clinic has) can be used as a mount for embodiments. Then, the mount can be brought extra-orally to its appropriate place and the intraoral source will track the mount and irradiate the appropriate area of the mouth.

Although specific embodiments have been described, it is evident that many alternatives, modifications and variations will be apparent to those skilled in the art. Accordingly, it is intended to embrace all such alternatives, modifications and variations that fall within the spirit and broad scope of the appended claims. In addition, citation or identification of any reference in this application shall not be construed as an admission that such reference is available as prior art.

We claim:

1. An intraoral radiation device compatible with oral cavities, comprising a biocompatible intraoral receptacle with an X-ray source therein, wherein the intraoral receptacle is fixedly mountable in an oral cavity, wherein the intraoral radiation device further comprises a power source operationally coupled to the X-ray source, wherein the intraoral receptacle has an inner side, wherein the X-ray source comprises an X-ray tube encapsulated within a housing, and wherein the housing is mounted on a hinge affixed to the inner side of the intraoral receptacle.

2. The device of claim 1, wherein the power source is enclosed within the receptacle.

3. The X-ray device of claim 1, wherein the intraoral receptacle is disposable.

4. The device of claim 1, wherein the intraoral receptacle is configured to allow performing therewith bite-wing dental scans.

5. The device of claim 1, wherein the X-ray source comprises:
   a high-Voltage circuit, comprising two electrodes with high-Voltage therebetween; and
   an electron-source circuit configured to emit electrons when inserted into an electric field.

6. The device of claim 5, wherein the X-ray source further comprises a high-Voltage capacitor.

7. The device of claim 6, wherein the X-ray source further comprises a set of Voltage multipliers.

8. The device of claim 1, wherein the X-ray source further comprises:
   an electron source;
   a thin high-z anode, having a transmission geometry; and
   a set of deflection plates configured to allow electron-beams from the electron source to be focused toward the anode,
   wherein the X-ray source is configured to allow acceleration and deflection of electrons from an X-ray emitter.

9. The device of claim 8, wherein the electron source comprises a plurality of carbon nano-tubes.

* * * * *